(12) United States Patent
Schäfer

(10) Patent No.: US 6,673,073 B1
(45) Date of Patent: Jan. 6, 2004

(54) TRANSVERSE CONNECTOR

(76) Inventor: Bernd Schäfer, Eggstrasse 27, CH-6315 Oberägeri (CH)

( * ) Notice: Subject to any disclaimer, the term of this patent is extended or adjusted under 35 U.S.C. 154(b) by 335 days.

(21) Appl. No.: 09/712,240

(22) Filed: Nov. 15, 2000

(30) Foreign Application Priority Data

Nov. 29, 1999 (DE) .......................................... 199 57 332

(51) Int. Cl.⁷ .............................................. A61B 17/58
(52) U.S. Cl. .......................................... 606/61; 606/60
(58) Field of Search ................................ 606/60, 61, 62

(56) References Cited

U.S. PATENT DOCUMENTS

| 5,413,576 | A | * | 5/1995 | Rivard | 606/61 |
|---|---|---|---|---|---|
| 5,545,164 | A | * | 8/1996 | Howland | 606/61 |
| 5,601,554 | A | * | 2/1997 | Howland et al. | 606/61 |
| 5,643,260 | A | * | 7/1997 | Doherty | 606/61 |
| 5,676,665 | A | * | 10/1997 | Bryan | 606/61 |
| 5,716,355 | A | * | 2/1998 | Jackson et al. | 606/61 |
| 5,800,548 | A | * | 9/1998 | Martin et al. | 623/17 |
| 6,096,039 | A | * | 8/2000 | Stoltenberg et al. | 606/61 |
| 6,387,097 | B1 | * | 5/2002 | Alby | 606/61 |

* cited by examiner

Primary Examiner—Linda C. M. Dvorak
Assistant Examiner—Aaron Roane
(74) Attorney, Agent, or Firm—Paul Vincent

(57) ABSTRACT

The invention concerns a transverse connector for osteosynthesis for interconnecting one or several vertebrae, wherein the transverse connector comprises a rod-shaped section for mounting same, and a clamping section for connection of the fixation rod.

12 Claims, 1 Drawing Sheet

TRANSVERSE CONNECTOR

This application claims Paris Convention priority of DE 199 57 332. 8 filed Nov. 29, 1999 the complete disclosure of which is hereby incorporated by reference.

BACKGROUND OF THE INVENTION

The invention concerns a transverse connector for osteosynthesis for connection of a fixation rod interconnecting several vertebrae.

Curvatures of the spine are conventionally treated by interconnecting several vertebrae via a fixation rod and are thus correctly positioned. Towards this end, pedicle screws are screwed into the vertebrae or bone plates are disposed on the vertebrae into which the fixation rod or, optionally, several fixation rods are introduced. With extreme curvatures of the spine, the curvature of the fixation rod may not be sufficient for binding the vertebrae, the bone screws screwed into the vertebra, or the disposed vertebrae plates to the fixation rod. For such curvatures of the spine, several fixation rods, which are connected to one another, must normally be used so that several bone screws have to be screwed into the individual vertebrae. This can cause problems since the strength of the vertebrae suffers.

It is therefore the underlying purpose of the present invention to provide a transverse connector which can also correct extremely curved spines.

SUMMARY OF THE INVENTION

This object is achieved in accordance with the invention with a transverse connector for osteosynthesis, wherein the transverse connector comprises a rod-shaped section to fix same and a clamping section for connecting the fixation rod.

The transverse connector in accordance with the invention facilitates use of fixation rods which are less curved even in the event of extremely curved spines, wherein the fixation rods are connected to the bone screws or bone plates and thus to the vertebrae via the transverse connector in accordance with the invention should direct connection of the fixation rod to the bone screws or bone plates not be possible. The transverse connector in accordance with the invention can thus safely transfer, without play, the correction forces from the fixation rod to the corresponding vertebrae. The transverse connector is connected either to the bone screw or to the bone plate via the rod-shaped section, wherein the fixation rod is mounted to the transverse connector via the clamping section.

A further development provides that the clamping section has an opening for receiving the fixation rod, said opening having a slot which is open at an edge. The fixation rod is guided through the opening and retained by reducing the cross-section of the opening after insertion of the fixation rod. This is usually effected by screwing in a screw to reduce the size of the slot and thereby clamp the fixation rod in the opening. It is also possible to screw a fixation screw into the clamping section which directly engages and holds the fixation rod. Clamping screws of this type are usually designed as stud screws.

In a preferred manner, the clamping section is formed in two pieces, with a clamping lid. The clamping lid thereby forms part of the opening for the fixation rod. This embodiment of the clamping section has the essential advantage that the fixation rod can be inserted into the opening in a relatively simple fashion and that the clamping lid is disposed only after insertion or introduction of the fixation rod to thereby close the opening.

The clamping lid is disposed on the rod-shaped section in a preferably pivotable fashion. The fixation rod can be removed relatively easily by pivoting open the opening and the opening is closed after insertion of the fixation rod by pivoting closed the clamping lid, as mentioned above.

In a preferred embodiment, the clamping lid has a shackle surrounding the rod-shaped section of the transverse connector thereby securely retaining the clamping lid. Moreover, the shackle transfers the clamping and retaining forces of the clamping lid to the rod-shaped section.

An embodiment provides that the shackle bends away from the plane of the clamping lid through an angle of about 900° and surrounds the rod-shaped section orthogonally to its longitudinal axis. This embodiment of the shackle permits pivoting or raising of the clamping lid while facilitating optimum force introduction and fixation of the clamping lid on the rod-shaped section.

To produce a defined position of the clamping lid, the shackle comprises a shoulder forming a bearing which is supported on a counter bearing of the other part of the clamping section. The two parts of the opening into which the fixation rod is inserted are also aligned with respect to one another via these two bearing parts.

In a preferred fashion, the bearing with associated counter bearing and the clamping screw are disposed on opposite sides of the opening for the fixation rod. The shackle surrounding the rod-shaped section is also disposed on the side of the bearing with associated counter bearing. This embodiment guarantees that even large forces can be easily introduced from the fixation rod into the transverse connector without changing the position of the fixation rod in the clamping section.

Further fixation against displacement and/or turning of the transverse connector in the bone screw or the bone plate is provided when the rod-shaped section has a surface structure having, in particular, grooves extending in the longitudinal direction. A surface structure, in particular comprising grooves extending in the longitudinal direction of the opening, can furthermore be provided on at least sections of the inner surface of the opening for the fixation rod. This surface structure prevents change of the position of the structural component in the associated clamping element. Other surface structures, such as fluting, a threaded structure etc. are also feasible.

In order to be able to easily use both fixation rods as well as the inventive transverse connector on the same bone screws and/or bone plates, the diameter of the rod-shaped section corresponds to the diameter of the opening for the fixation rod, wherein the transverse connector does not require any special bone screws and/or bone plates.

Surgery is facilitated when the clamping section has a securely fastened screw. This precludes parts of the transverse connector from becoming lost after insertion of the transverse connector and before the final clamping of the fixation rod. The screw for mounting the clamping lid is always securely retained on the clamping lid.

Further advantages, features and details of the invention can be extracted from the dependent claims and the following description describing, in detail, a particularly advantageous embodiment with reference to the drawing. The features shown in the drawing and mentioned in the claims and the description may be essential to the invention either individually or collectively in any arbitrary combination.

DESCRIPTION OF THE PREFERRED EMBODIMENT

Figure 1:
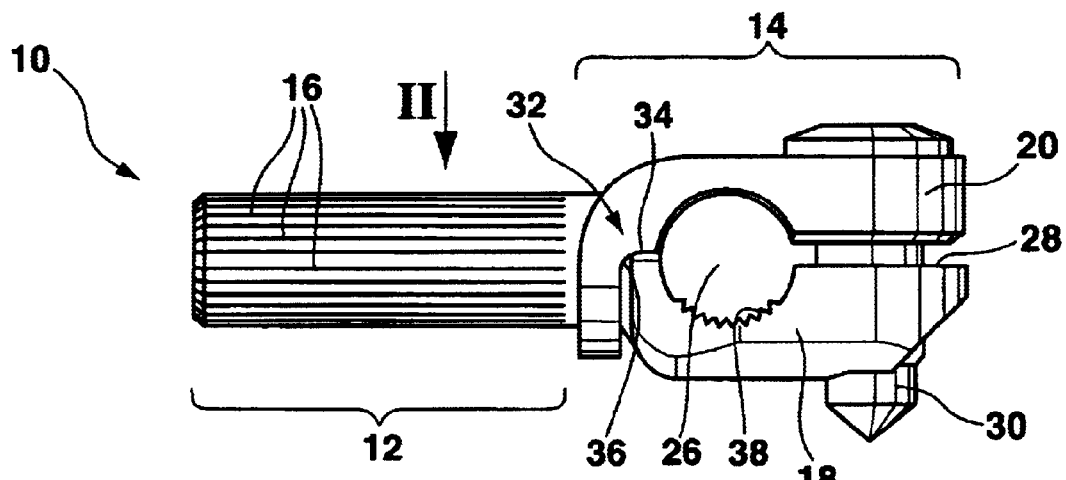
FIG. 1 shows a side view of the transverse connector in accordance with the invention.
Figure 2:
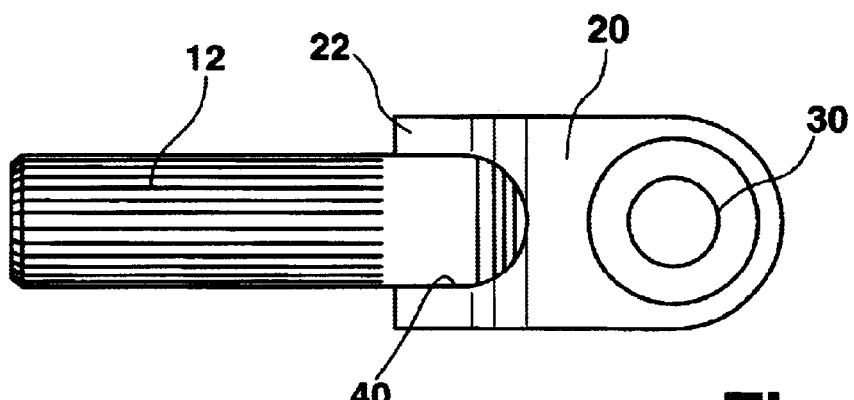
FIG. 2 shows a top view of the transverse connector in the direction of the arrow II in accordance with FIG. 1.

FIG. 1 shows a preferred embodiment of a transverse connector 10 in accordance with the invention. This transverse connector 10 is formed by a rod-shaped section 12 and a clamping section 14. The rod-shaped section 12 of the transverse connector 10 is connected to e.g. a bone screw (not shown) or a bone plate (not shown). The cross-section of the rod-shaped section 12 thereby corresponds essentially to the cross-section of a fixation rod (not shown) for correcting curvatures of the spine. This rod-shaped section 12 has a round cross-section having grooves 16 extending on the outer side in the longitudinal direction to prevent rotation.

Figure 3:
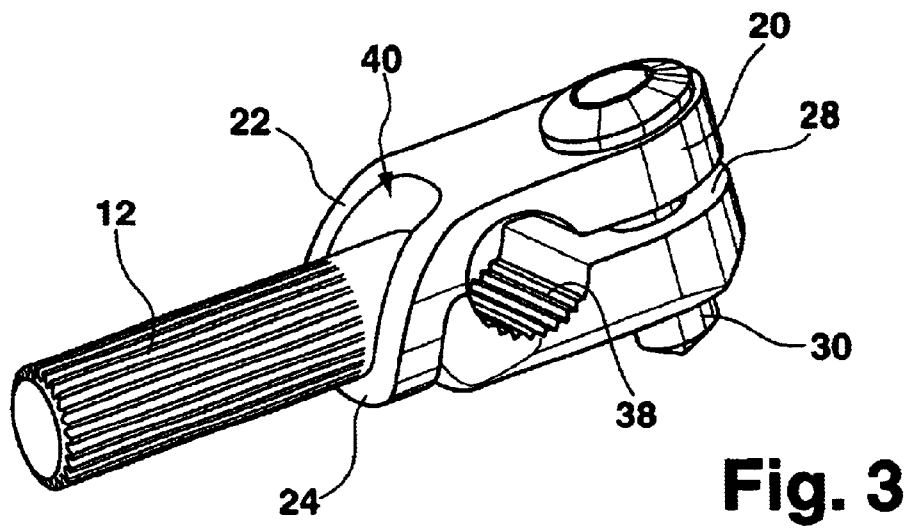
FIG. 3 shows a perspective view of the transverse connector.

The clamping section 14 is formed from two parts and comprises a first part 18 integral with the rod-shaped section 12. The second part is formed as clamping lid 20 and is disposed on the rod-shaped section 12 in a pivotable fashion. As clearly shown, in particular in FIG. 3, the clamping lid 20 comprises a shackle 22 surrounding the rod-shaped section 12, which is angled through 900° in a curved manner and away from the plane of the clamping lid 20 and is disposed with its end 24 opposite the clamping lid 20 essentially orthogonal to the longitudinal axis of the rod-shaped section 12.

The clamping lid 20 and the first part 18 of the clamping section 14 form an opening 26 having a slot 28 open at the edge. The fixation rod (not shown) is inserted into the opening 26 and clamped. Clamping is effected by screwing a clamping screw 30, rigidly retained in the clamping lid 20, into a corresponding threaded opening in the first part 18. The clamping lid 20 is clamped onto the fixation rod by means of the clamping screw 30. The clamping lid 12 is thereby pivoted about a pivoting bearing 32 formed by a shoulder 34 and a counter bearing 36.

To be able to securely fix the fixation rod in the clamping section 14, the opening 26 comprises longitudinal grooves 38 in its axial direction which are provided on part of the inner circumference of the opening 26.

Easy insertion of the fixation rod into the clamping section 14, even if the transverse connector 10 is mounted to the bone screw, is effected by pivoting the pivoting lid about the pivoting bearing 32 after unscrewing the clamping screw 30. The rod-shaped section 12 thereby pivots in a kidney-shaped opening 40 surrounded by the shackle 22. The fixation rod can be easily inserted into the open opening 26. Fixation is effected by pivoting the clamping lid 20 and securing the clamping screw 30 to the first part 18.

In an embodiment not shown in the drawing, the clamping section 14 is formed as a single piece, i.e. the clamping lid 20 is integral with the first part 18. The opening 26 thereby tapers and holds an inserted clamping rod through elastic deformation of the clamping section 14 by screwing in the clamping screw 30. In this embodiment, the transverse connector 10 has to be pushed onto the fixation rod before fixing same on the bone screws or bone plates.

I claim:

1. A transverse connector for osteosynthesis to capture a fixation rod interconnecting several vertebrae, the connector comprising:
    a rod-shaped section for mounting the connector;
    a clamping section for connecting the fixation rod, wherein the clamping section has an opening receiving the fixation rod, said opening having a slot, open at an edge thereof, said clamping section being formed as a clamping lid and a clamping piece, said clamping lid comprising a shackle surrounding said rod-shaped section; and
    a clamping screw disposed on a side of said opening opposite said shackle.

2. The transverse connector of claim 1, wherein said clamping lid defines a part of said opening for the fixation rod.

3. The transverse connector of claim 1, wherein said clamping lid is pivotably disposed on said rod-shaped section.

4. The transverse connector of claim 1, wherein said shackle is bent through substantially 90° away from a plane of said clamping lid to surround said rod-shaped section orthogonally to a longitudinal axis thereof.

5. The transverse connector of claim 1, wherein said shackle comprises a shoulder forming a bearing which is supported on a counter bearing of said clamping piece.

6. The transverse connector of claim 1, wherein said rod-shaped section has a first surface structure.

7. The transverse connector of claim 6, wherein said first surface structure comprises grooves extending in a longitudinal direction of said rod-shaped section.

8. The transverse connector of claim 1, wherein at least sections of an inner surface of said opening are provided with a second surface structure.

9. The transverse connector of claim 8, wherein said second surface structure comprises grooves extending in a longitudinal direction of said opening.

10. The transverse connector of claim 1, wherein a diameter of said rod-shaped section corresponds to a diameter of said opening.

11. The transverse connector of claim 1, wherein said clamping section comprises a securely mounted screw.

12. The transverse of claim 1, wherein the connector is made from at least one of stainless steel and titanium.

* * * * *